(12) United States Patent
Zardini

(10) Patent No.: US 9,586,242 B2
(45) Date of Patent: Mar. 7, 2017

(54) PERFECTED WASHING PLANT

(75) Inventor: Fabio Zardini, Castelfranco Veneto (IT)

(73) Assignee: STEELCO SPA, Riese Pio X (IT)

( * ) Notice: Subject to any disclaimer, the term of this patent is extended or adjusted under 35 U.S.C. 154(b) by 681 days.

(21) Appl. No.: 13/992,479

(22) PCT Filed: Oct. 31, 2011

(86) PCT No.: PCT/IB2011/002616
§ 371 (c)(1),
(2), (4) Date: Aug. 21, 2013

(87) PCT Pub. No.: WO2012/076944
PCT Pub. Date: Jun. 14, 2012

(65) Prior Publication Data
US 2013/0319475 A1    Dec. 5, 2013

(30) Foreign Application Priority Data

Dec. 10, 2010 (IT) .............................. UD2010A0227

(51) Int. Cl.
*B08B 1/02* (2006.01)
*B08B 7/04* (2006.01)
(Continued)

(52) U.S. Cl.
CPC *B08B 7/04* (2013.01); *A61L 2/04* (2013.01); *A61L 2/24* (2013.01); *B08B 3/04* (2013.01);
(Continued)

(58) Field of Classification Search
None
See application file for complete search history.

(56) References Cited

U.S. PATENT DOCUMENTS 6,959,714 B1    11/2005   Håkansson et al.
2007/0205081 A1    9/2007   Kyutoku et al.
(Continued)

FOREIGN PATENT DOCUMENTS

EP    1787662    11/2006
EP    1787662    5/2007
(Continued)

OTHER PUBLICATIONS

Notice of Opposition of EP 11796803.2-1356 / 2648769 dated May 4, 2015, 32 pages.
(Continued)

*Primary Examiner* — Binh X Tran
*Assistant Examiner* — David Cathey, Jr.
(74) *Attorney, Agent, or Firm* — Rankin, Hill & Clark LLP

(57) ABSTRACT

A washing plant (10) comprises a battery (12) of washing and heat-disinfection machines (14, 16, 18) disposed along an alignment axis (X), able to operate in parallel with respect to each other in order to effect the washing and heat-disinfection, at least a translator slider (20) mobile in an automatic manner parallel to the alignment axis (X) in a front position to said battery (12), which receives the objects to be washed and both transports them in correspondence to the entrance of one of the machines (14, 16, 18) selected on each occasion depending on the washing program set or depending on availability, and moves them inside the desired machine (14, 16, 18) in a direction of feed (F) substantially perpendicular to said alignment axis (X), transport means (24) being provided to direct the objects to be washed toward the translator slider (20) operating in a direction of transport (Y) substantially parallel to said alignment axis (X). The translator slider (20) comprises a lower frame (22) associated slidably to the battery (12) of machines (14, 16,
(Continued)

18), in order to allow the movement parallel to the alignment axis (X), and a rotating upper frame (32) suitable to support the objects to be washed and which comprises movement means (34) to move the objects inside the desired machine (14, 16, 18) in said direction of feed (F), said rotating upper frame (32) being rotatably coupled to the lower frame (22) by means of rotation means (42), so as to be able to be rotated between a first position, aligned to said direction of transport (Y) of the transport means (24) and in which it is configured to receive the objects from said transport means (24), and a second position, aligned to said direction of feed (F) to direct the objects inside the desired machine (14, 16, 18).

7 Claims, 3 Drawing Sheets

(51) Int. Cl.
    *A61L 2/04*     (2006.01)
    *A61L 2/24*     (2006.01)
    *B08B 13/00*     (2006.01)
    *B08B 3/04*     (2006.01)

(52) U.S. Cl.
    CPC ........... *B08B 13/00* (2013.01); *A61L 2202/16* (2013.01); *A61L 2202/17* (2013.01); *A61L 2202/24* (2013.01)

(56) References Cited

U.S. PATENT DOCUMENTS

| | | | |
|---|---|---|---|
| 2010/0206335 A1* | 8/2010 | Zardini | A61L 2/04 134/19 |
| 2011/0238201 A1 | 9/2011 | Hiroki | |

FOREIGN PATENT DOCUMENTS

| | | |
|---|---|---|
| EP | 1787731 | 5/2007 |
| JP | 2010147207 | 7/2010 |
| JP | 2010537753 | 12/2010 |
| WO | 2009030599 | 3/2009 |

OTHER PUBLICATIONS

Medienmitteilllig des Kantonsspitals Aarau vom 3. Apr. 2009, 1 page, cited in Notice of Opposition.
Verfügung mit Begleitbrief des Kantonsspitals Aarau vorn 7. Jan. 2008 betreffend Submissions-ergebnis, 3 pages, cited in Notice of Opposition.
Auftragsbestatigung Nr. 105840-1 der Belimed Sauter AG an das Kantonsspitals Aarau vom 12. Feb. 2008, 10 pages, cited in Notice of Opposition.
Aufstellungszeichnung "7 x WD29O" für die zentrale Sterilgutversorgungsabteilung (ZSVA) am Kantonsspital Aarau vom 15. Sep. 2008, 1 page, cited in Notice of Opposition.
Konvolut von 11 Arbeitsberichten der Belimed Sauter AG (Herr Urs Gyger) vom 5. Dec. 2008 bis zum 30. Apr. 2009, 11 pages, cited in Notice of Opposition.
3 Farbfotographien der zentralen Sterilgutversorgungsabteilung (ZSVA) am Kantonsspital Aarau während der Umbauphase, 2 pages, cited in Notice of Opposition.
Rechnung Nr. RAD 29002338 der Belimed Sauter AG an das Kantonsspitals Aarau vom 31. Mar. 2009, 10 pages, cited in Notice of Opposition.
Prüfprotokoll der Übergabe beim Kunden vom 7. May 2009, erstellt durch Belimed Sauter AG, unterzeichnet durch Herr P. Hohl, Kantonsspital Aarau, 3 pages, cited in Notice of Opposition.
Arbeitsbericht über Instruktion und Schulung der Belimed Sauter AG vom 13. May 2009, 1 page, cited in Notice of Opposition.
Unternehmensschlussabrechnung an das Kantonsspital Aarau durch Belimed Sauter AG vom 31. Aug. 2009, 1 page, cited in Notice of Opposition.
Bedienungsanleitung Rotary der Belimed AG, 25 pages, cited in Notice of Opposition.
Technisches Handbuch Rotary der Belimed AG, 60 pages, cited in Notice of Opposition.
Artikel der Aargauer Zeitung vom 4. Apr. 2009 "Eine der rnodernsten Anlagen in ganz Europa.", 3 pages, cited in Notice of Opposition.
Messekonzept von Belimed für die Medica 2007, 13 pages, cited in Notice of Opposition.
Formular Messebericht Medica 2007 über ein Gesprach mit einem Interessenten betreffend WD290 und Rotary-System, 1 page, cited in Notice of Opposition.
Farbfotographie des Standes von Belimed an der Medica 2007 mit zwei WD 290 (ausgestattet mit Rotary-System) im Vordergrund, 1 page, cited in Notice of Opposition.
Warenliste für die gelieferten Gerate an die Medica 2007 umfassend zwei Reinigungs-, Desinfektions- und Trocknungsautomaten WD290 sowie, vier Rotary Module, 1 page, cited in Notice of Opposition.
Plan Rotary-System für Medica 2007, 1 page, cited in Notice of Opposition.
Eidesstattliche Erklärung Philipp Küttel, 4 pages, cited in Notice of Opposition.
Notification of Reason(s) for Refusal of JP Application No. 2013-542621 dated Jun. 3, 2015, pages.
Notification of Reason(s) for Refusal of JP Application No. 2013-542621 dated Jun. 3, 2015, 3 pages, English translation.
International Search Report of PCT/IB2011/002616 dated Jan. 25, 2012.

\* cited by examiner

PERFECTED WASHING PLANT

FIELD OF THE INVENTION

The present invention concerns a washing plant for objects, for example medical instruments for hospital wards, operating rooms, laboratories and the pharmaceutical industry, typically contained in a rack, comprising a first battery of washer machines, aligned in a desired first direction so as to operate in parallel, and comprising a translator slider mobile in the first direction so as to feed one or more racks containing objects to be washed to one of the washer machines selected on each occasion according to the washing program set, or according to availability. The racks containing the objects to be washed supplied to the translator slider typically come from transport and feed means, which can be automatic, semi-automatic or manual, generally associated with a second battery of pre-wash machines aligned on a determinate axis of alignment so as to operate in series.

BACKGROUND OF THE INVENTION

It is known that, usually, hospital structures are provided with a washing plant to pre-wash, wash, heat disinfect and sterilize objects, such as for example instruments used in the operating rooms and hence potentially infected and not sterile, before they are able to re-use them.

In particular, known washing plants are normally divided into several sectors, isolated from each other for reasons of hygiene and respectively called "dirty" or reception sector, "clean" sector and "sterile" sector.

In the first sector, that is, the dirty one, the racks containing the dirty objects to be subjected to the various treatments arrive. The treatments carried out are, generally speaking, a pre-wash with cold water only, a possible wash in an ultrasound bath, a hot water wash with possible detergents, the necessary rinses, heat-disinfection and final drying. In particular, heat-disinfection, which is a particular type of washing, is carried out with hot water, usually at a temperature comprised between about 90° C. and about 93° C.

Usually the pre-wash is carried out by means of a battery of suitable pre-wash machines or units, for example two or three, disposed aligned on a determinate axis of alignment, so as to operate in series with each other.

The cycle that provides washing, rinsing, heat-disinfection and drying is carried out on the contrary in a battery of suitable washer machines, for example five or six, according to the productivity needs, aligned on a respective axis of alignment, so as to operate in parallel with each other.

The racks with the objects to be washed are taken at exit from the last pre-wash unit and fed to the washing and heat-disinfection machine available at that moment.

Each washing and heat-disinfection machine, since it operates in parallel with the other washer machines and consists of a washing chamber with an opening facing toward the dirty side and an opposite opening facing toward the clean side, must be fed in a direction that is orthogonal to its axis of alignment with the other washing and heat-disinfection machines. Normally, the feed is effected by means of a translator slider mobile in the direction of alignment of the washer machines, which receives the racks containing the objects to be washed at exit from the pre-wash battery, or from a loading station. The translator slider transports them in correspondence with the entrance to one of the washer machines selected on each occasion according to the washing program set, or according to availability, and also moves them inside the desired washer machine in the direction of feed.

On the contrary, in the pre-wash units, which operate in series, the direction of feed coincides with the axis of alignment along which the pre-wash battery develops.

Normally, therefore, the second washing and heat-disinfection battery is disposed downstream of the pre-wash battery and with its axis of alignment perpendicular to the axis of alignment of the pre-wash battery. Therefore, the axis of alignment of the pre-wash units is orthogonal to the axis of alignment of the washing and heat-disinfection machines. In this way the objects exiting from the last pre-wash unit are ready to be sent directly to the washing and heat-disinfection machines.

Some examples of this embodiment of such washing plants can be found in the European patent applications EP-A-1.787.662 and EP-A-1.787.731 in the name of the present Applicant.

After being heat disinfected and dried, the objects pass to the second clean sector in which they are possibly packed and from here are fed to a battery of sterilization machines, generally autoclaves, which sterilize them; they operate in parallel and are typically aligned in a direction parallel to the washing and heat-disinfection battery.

The objects thus sterilized pass to the following third sterile sector where they are stored or again sent for use in the operating room.

One disadvantage of known washing plants is that, in order to carry out at least the pre-wash and the washing and heat-disinfection, they have very large installation sizes.

To overcome this disadvantage, a compact plant is known from the international application WO-A-2009/030599, in the name of the Applicant, where the axis of alignment of the pre-wash units is substantially parallel to the axis of alignment of the washer machines, with switching means being provided directly at exit from the pre-wash battery, which direct the racks with the objects in the suitable direction of feed to the washer machines. The racks containing the objects to be washed, once correctly directed, are translated on movement means of the fixed type which operate by displacing the racks in the direction of feed toward the translator slider, where they are then moved as described above.

However, this known solution too, in particular contexts where the installation spaces of the plant are narrow or not optimal, may suffer from an excessive bulk.

Purpose of the present invention is to achieve a perfected washing plant that takes up little space, that is compact and allows an easy passage of the objects to be washed to the washing and heat-disinfection machines.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purpose, a washing plant according to the present invention is used to effect at least a washing cycle on objects, typically contained in racks, which provides at least a washing and heat-disinfection operation.

The plant according to the present invention comprises a battery of washing and heat-disinfection machines disposed along an axis of alignment, able to operate in parallel with respect to each other so as to effect the washing and heat-disinfection.

The plant comprises at least a translator slider mobile automatically and parallel to the axis of alignment in a front position to the battery, which receives the objects to be washed, for example contained in racks, and both transports them in correspondence with the entrance to one of the washer machines selected on each occasion according to the washing program set, or according to availability, and also moves them inside the desired washer machine in a direction of feed substantially perpendicular to the axis of alignment.

According to the present invention, transport means are provided which direct the objects to be washed toward the translator slider in a direction of transport substantially parallel to the axis of alignment.

Furthermore, the translator slider comprises a lower frame slidingly associated with the battery of washer machines, to allow the movement parallel to the axis of alignment of the washer machines, and a rotating upper frame suitable to support the objects to be washed and which comprises movement means to move the objects inside the desired washer machine in the direction of feed.

The rotating upper frame is rotatably coupled with the lower frame by rotation means, so that it can be rotated between a first position, aligned with the direction of transport of the transport means and in which it is configured to receive the objects from the transport means, and a second position, aligned with the direction of feed to direct the objects inside the washer machines. The rotation into the second position can occur before, after or during the movement of the translator slider parallel to the axis of alignment of the battery of washer machines.

In some forms of embodiment of the present invention, advantageous if the rotating upper frame of the translator slider has a conformation with a development mainly in the direction of feed, for example if it has a rectangular design with the long sides parallel during use to the direction of feed, the lower frame and the rotating upper frame are also translatable linearly with respect to a common base support frame typically disposed on a support plane of the plant, parallel to the direction of feed by means of linear movement means mounted on the translator slider, between a third position close to the washer machines, in which the movement is allowed of the objects inside the washer machines, and a fourth position, distanced from the washer machines, so as to define a maneuvering interspace for the rotation of the rotating upper frame.

In this way, before rotating the rotating upper frame with respect to the lower frame, it is possible to translate linearly backward the combination formed by the lower frame and the rotating upper frame so as to create the space needed to rotate the bulk of the rotating upper frame without it interfering with other front parts of the slider or the washer machines. The rotating upper frame, after being moved backward in the fourth position, can be rotated from the first to the second position without interfering with other parts of the slider or the machines, and then can be loaded with the objects to be washed received from the transport means, again rotated from the second to the first position and subsequently made to advance again toward the washer machines in the third position.

It is thus possible to install the plant even in very narrow spaces or with an elongated conformation, since the bulk of the fixed movement means, normally disposed between the pre-wash and the washer machines perpendicular to the axis of alignment of the latter, is completely eliminated.

In fact, by disposing the movement means with an operating direction parallel to the axis of alignment of the washer machines and in direct cooperation with the movement path of the translator slider, it is possible to load the objects easily onto the translator slider, where the rotating upper frame has been suitably rotated in the direction coordinated with the movement means and, subsequently, to direct the objects to the washer machines, by means of the translator slider, where the rotating upper frame has again been rotated in the direction coordinated with the direction of feed toward the washer machines.

In some forms of embodiment, the plant according to the present invention comprises another translator slider cooperating with transport means provided on the rear side at exit from the battery of washer machines.

The other translator slider is mobile automatically parallel to the axis of alignment in a rear position behind the battery so as to receive the washed objects exiting from the battery of machines, and to move them to the transport means, which provide to direct them to other treatments, or to packaging and/or storage. The other translator slider comprises a lower frame and a rotating upper frame which is made rotatable by means of rotation means between a position aligned with the direction of feed so as to withdraw the objects exiting from inside the desired machine, and a position aligned with the direction of transport of the transport means and in which it is configured to direct the objects to the transport means.

In some forms of embodiment, the lower frame and the rotating upper frame of the other translator slider are also translatable linearly parallel to the direction of feed between a position close to the machines, and a position distanced from the machines, so as to define a maneuvering interspace for the rotation of the rotating upper frame.

According to some forms of embodiment, the plant according to the present invention comprises a dirty sector defined between first main separation means and the battery of machines, in which the transport means and the translator slider are provided, and a clean sector in which the other transport means and translator slider are provided. The clean sector is defined between the battery of machines and second main separation means, in a position opposite and substantially parallel to the first main separation means, and is separated from the dirty sector by means of the battery of machines and by secondary separation means.

In some forms of embodiment, the first main separation means are disposed at a reciprocal distance from each other, given substantially by the sum of the length of the translator slider, the depth of the battery of machines and the necessary interspace provided for the rotation of the rotating upper frames.

The present invention also concerns a method to carry out at least one washing cycle on objects, which provides at least a washing and heat-disinfection operation performed by a battery of washing and heat-disinfection machines disposed along an axis of alignment, which operate in parallel with respect to each other to perform the washing and heat-disinfection. In the method according to the present invention the objects to be washed are transported by transport means in a direction of transport substantially parallel to the axis of alignment, a translator slider receives the objects to be washed arriving from the transport means and moves them automatically parallel to the axis of alignment in a front position to the battery, transporting them in correspondence with the entrance to one of the machines selected on each occasion according to the washing program set or according to availability, and moves them inside the desired machine in a direction of feed substantially perpendicular to the axis of alignment.

According to the method of the present invention, the objects are loaded onto the translator slider operating in a first position of alignment with the direction of transport and before, after or during the movement of the translator slider parallel to the axis of alignment the objects are rotated, remaining disposed on the translator slider, into a second position, aligned with the direction of feed so as to direct the objects inside the desired machine.

In some forms of embodiment of the present invention, the method provides to withdraw, or unload, the washed objects in symmetry with the loading operation. In particular, the objects are unloaded onto a translator slider at exit from the washer machines, operating in a direction aligned with the direction of feed, and are moved automatically together with the translator slider, parallel to the direction of alignment of the battery of washer machines, toward the transport means able to receive them at exit. Before, after or during the movement of the objects, they are rotated, remaining disposed on the translator slider at exit, in coordination with the direction of transport associated with the transport means, so as to be directly usable by the transport means.

BRIEF DESCRIPTION OF THE DRAWINGS

These and other characteristics of the present invention will become apparent from the following description of a preferential form of embodiment, given as a non-restrictive example with reference to the attached drawings wherein.

Figure 1:
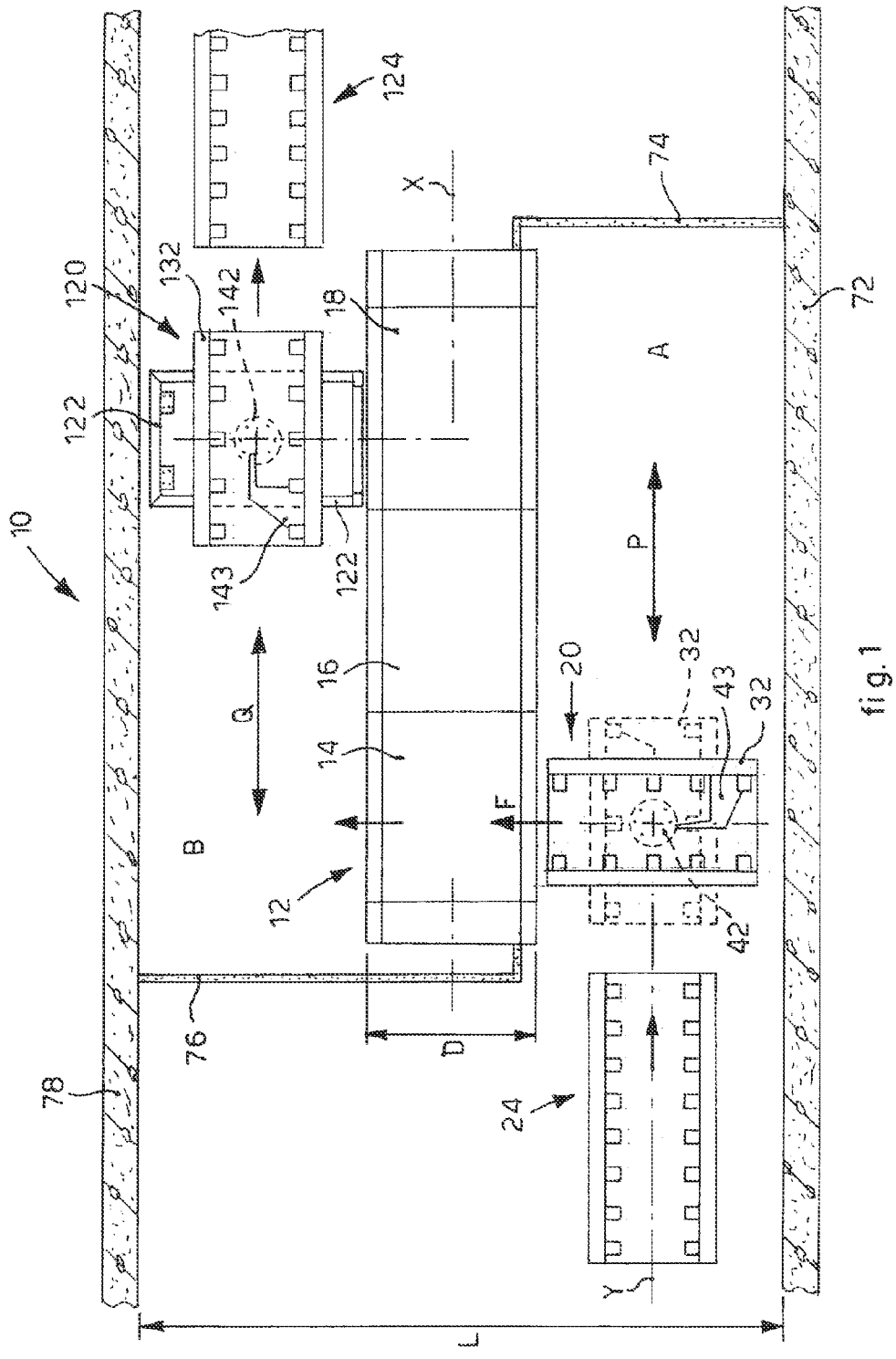
FIG. 1 is a plan view of a plant according to the present invention.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF A
PREFERENTIAL FORM OF EMBODIMENT

With reference to FIG. 1, a washing plant 10 according to the present invention is used to effect the complete treatment of pre-washing, washing, heat-disinfection and sterilization of objects, such as instruments from hospital wards, operating rooms, laboratories and the pharmaceutical industry, generally contained and transported in suitable racks.

The plant 10 in particular is configured in three sectors divided by separation means 72, 74, 76, 78, for example walls, possibly put selectively in communication by a passthrough, in particular a dirty sector A, to receive the dirty instruments, a clean sector B, downstream of the heat-disinfection, and a sterile sector, downstream of the sterilization.

The expression "separation means" means both separating walls proper, and also the bodies of other machines or apparatuses, and also paths needed for moving the instruments or other objects to be washed. For example, it is possible to provide two opposite main separation walls, a main separation wall and an object movement path which functions as a second main separation mean and secondary separation walls. Therefore the separation means, in the spirit of the invention, cannot be occupied since they physically prevent it, such as walls or machines, or must not be occupied because they are needed for other functions, such as the object movement paths.

In the dirty sector A, a battery may be provided consisting of pre-wash units, not shown, operating in series to effect a cold pre-wash, washing in possible chemical detergents and/or washing in an ultrasound bath, and disposed in different combinations and sequences, according to needs.

The expression "operating in series" means that the objects exiting from a pre-wash unit directly face toward the entrance to the pre-wash unit immediately following and thus constitute precisely the objects entering into the following pre-wash unit, except for the last pre-wash unit.

Between the dirty sector A and the clean sector B, the plant 10 comprises a battery 12 of washer machines 14, 16 and 18, aligned along an axis of alignment X and operating in parallel, in this case three, although there could be two or even more than three washer machines.

Finally, between the clean sector B and the sterile sector there are sterilization autoclaves provided, not shown, operating in parallel.

The expression "operating in parallel" means that the washing and heat-disinfection machines are adjacent and have their respective entrance openings to the internal washing chambers of the washer machines 14, 16, 18 disposed parallel to each other and on the same plane, so that the objects enter into one of the washing and heat-disinfection machines selected.

This means that the direction of travel and feed of the instruments to be washed along the battery 12, indicated by the arrow F, is substantially perpendicular to the axis of alignment X along which the washer machines 14, 16 and 18 are aligned.

The plant 10 comprises transport means of the fixed type by means of which the racks containing the instruments to be washed are transported toward the battery 12, in a direction of transport Y parallel to the axis of alignment X of the battery 12.

In the form of embodiment shown, the transport means comprise a roller-way 24, which develops mainly in a longitudinal direction along the direction of transport Y.

The plant 10 comprises a translator slider 20, disposed in the dirty sector A substantially in a front position with respect to the entrance to the washer machines 14, 16, 18.

The translator slider 20 is mobile, automatically, in a direction parallel to the axis of alignment X of the battery 12, as indicated by the arrow P in FIG. 1. It receives the objects to be washed from the transport means, in this case the rollerway 24, and transports them in correspondence with the entrance to one of the washer machines 14, 16, 18, selected on each occasion according to the washing program set or according to availability; it also moves them inside the desired washer machine 14, 16, 18 in the direction of feed F, substantially perpendicular to the axis of alignment X.

The transport means, in this case the rollerway 24, are disposed in an external position with respect to the path followed by the translator slider 20 in front of the washer machines 14, 16, 18, so as not to interfere with it, and at the same time in any case is positioned directly in correspondence with one of the ends of the battery 12 of the washer machines 14, 16, 18, so that it can easily supply the racks with the objects to be washed to the translator slider 20.

In some forms of embodiment, the translator slider 20 (FIG. 2) comprises a lower frame 22 slidingly associated with the battery 12 of washer machines 14, 16, 18 to allow to move the translator slider 20 parallel to the axis of alignment X, and a rotating upper frame 32 suitable to define a support plane to support the objects to be washed and which comprises movement means 34 to move the objects inside one of the washer machines 14, 16, 18 in the direction of feed F.

The rotating upper frame 32 is rotatably coupled with the lower frame 22 by means of rotation means 42, so that it can be rotated around its own vertical axis Z, as indicated by the arrow G (FIG. 2) between a first position, aligned with the direction of transport of the transport means 24 and in which it is configured to receive the objects from the transport means 24, and a second position aligned with the direction of feed F to direct the objects inside the washer machines 14, 16, 18.

According to a variant, the rotation means 42 can be made as described in the international application WO-A-2009/030599 in the name of the present Applicant, comprising a drum 42a, and a pair of attachment plates 42b, 42c of the horizontal type, parallel to each other and associated respectively to the lower frame 22 and the rotating upper frame 32. A linear actuator of the hydraulic type is mounted on the lower frame 22, having a rod mobile telescopically for a predetermined travel, whereas on the plate 42b, in particular on its lower face, the drum 42a is mounted, bearing at the center a cylinder able to rotate around its own axis and coupled at the upper part with the plate 42c. Below, the cylinder is keyed onto a lever, which has one end constrained to the rod of the linear actuator. The linear motion of the linear actuator, in particular the telescopic extension of the rod, suitably commanded and controlled, determines the rotation of the lever and consequently of the cylinder and the plate 42b solid therewith. The entity of the travel of the rod of the linear actuator is directly correlated to the angle of rotation to be imparted to the rotating upper frame 32. All this leads to the rotation, in this case by about 90°, of the rotating upper frame 32 and the rack with the objects to be washed.

The embodiment of the rotation means 42 as described above for the rotatable coupling of the lower frame 22 and the rotating upper frame 32 is not to be understood as limiting for the present invention, inasmuch as the present invention could be used in any other rotation mechanism that allows to rotate the rack carrying the instruments arriving from the rollerway 24 in the direction of transport Y in order to feed it in the direction of feed F.

In some forms of embodiment, the movement of the translator slider 20 at the front of the washer machines 14, 16, 18 and parallel to the axis of alignment X is made possible by motorization means, not shown.

The European patent applications EP-A-1.787.662 and EP-A-1.787.731 in the name of the present Applicant describe forms of embodiment to move the translator slider 20 automatically along the battery 12 of the washer machines 14, 16, 18.

In some forms of embodiment, to facilitate the movement of the translator slider 20, a guide bar 24 is provided, disposed below and in front of the machines 14, 16, 18, parallel to the axis of alignment X, with which an attachment portion 26, associated with the lower frame 22, is slidingly coupled.

Furthermore, the lower frame 22 can also be associated with a plurality of sliding means that cooperate with the support plane on which the plant 10 lies, in this case wheels 23, which can be clamped in a position coordinated with the movement parallel to the axis of alignment X, or can be revolving.

In some forms of embodiment, the translator slider 20, in design, has a development mainly in the direction of feed F, in this case a rectangular shape with the long sides disposed parallel to the direction of feed, in normal use, when feeding into the washer machines 14, 16, 18. The rectangular shape is selected to house, generally on several planes, a determinate number of racks which in turn contain the instruments to be washed and which have standardized sizes.

In particular, the rotating upper frame 32 has a rectangular shape and comprises two long sides 32a, opposite and parallel both to each other and also to the direction of feed F, distanced by two short sides 32b, opposite and parallel to each other and to the axis of alignment X.

In these forms of embodiment, the rotation of the rotating upper frame 32, due to the rectangular shape described above, could take the edges of the rotating upper frame 32 into interference with other front parts of the translator slider 20 and/or one of the washer machines 14, 16, 18. In fact, the translator slider 20, and in particular the rotating upper frame 32, are positioned near the battery 12 of washer machines 14, 16, 18 with which the translator slider 20 is mechanically coupled, to prevent, in some operating conditions, the distribution of the mass of instruments to be washed and the racks from being dangerously displaced from the barycenter.

Figure 2:
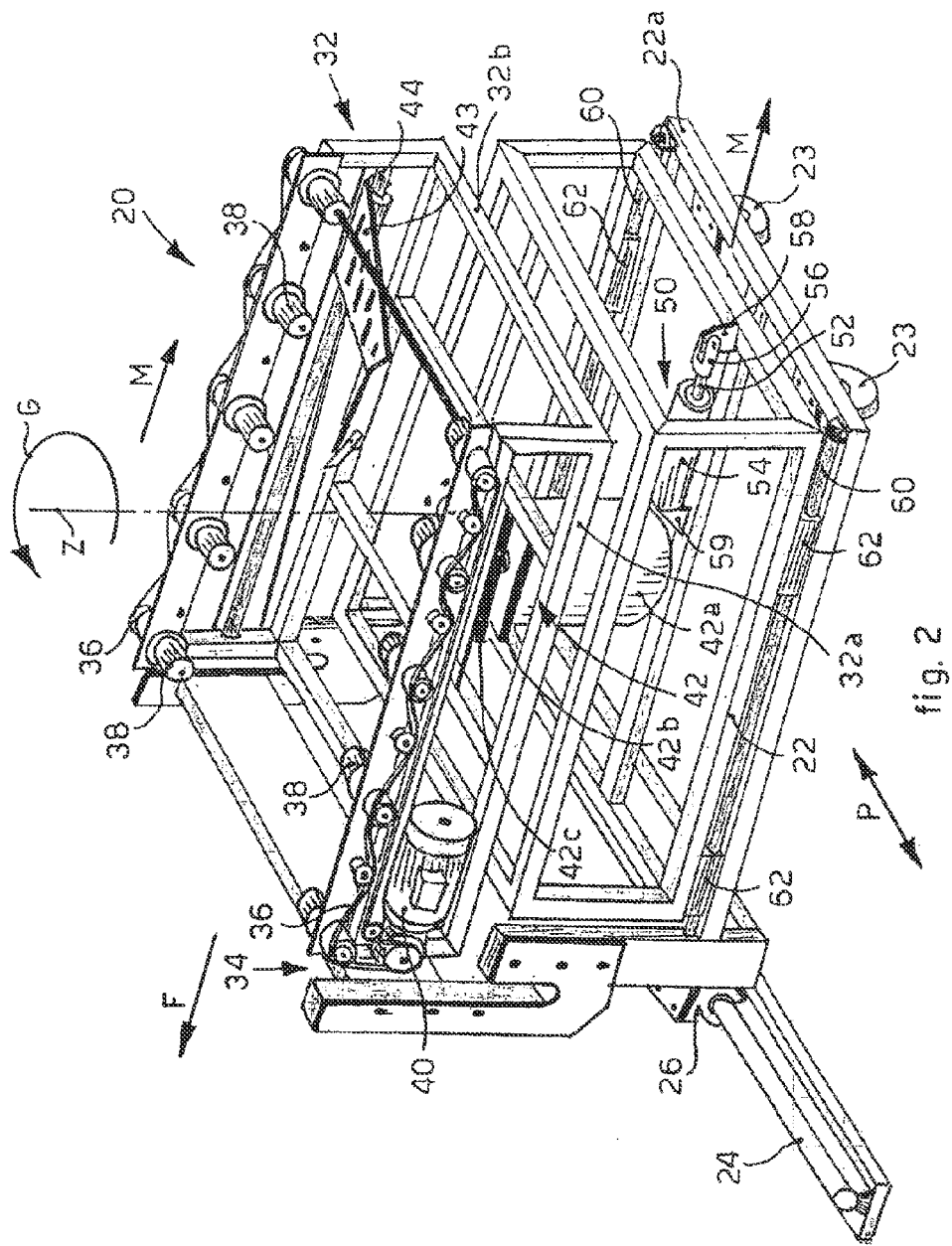
FIG. 2 is a perspective view of the translator slider of the plant in FIG. 1.
Figure 3:
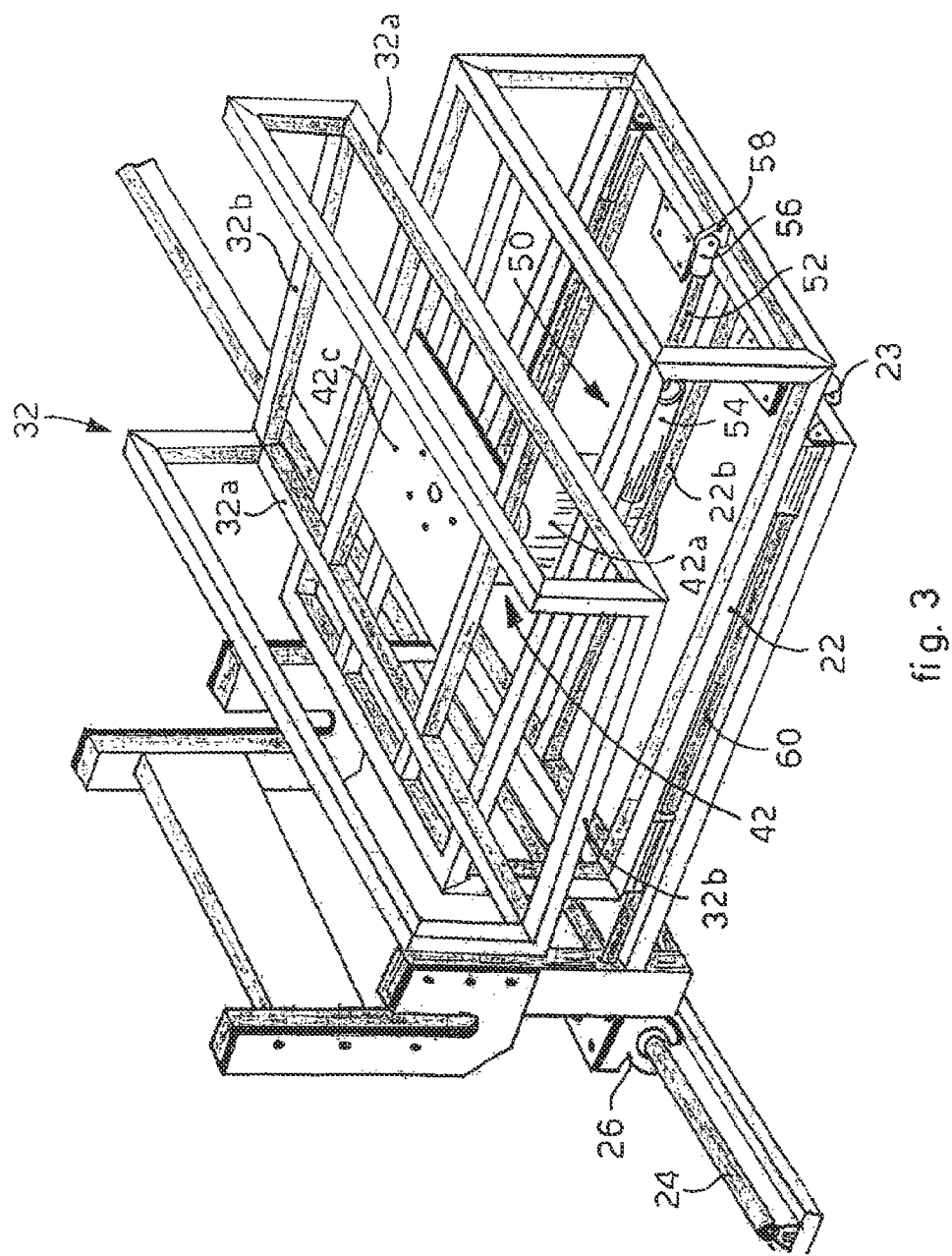
FIG. 3 is a perspective view of a part of the translator slider in FIG. 2 in a rotated and retracted position.

To prevent any obstacle to the rotation of the rotating upper frame 32, one form of embodiment of the present invention provides that the lower frame 22 and the rotating upper frame 32 are also translatable linearly with respect to a common base support frame 22a (FIGS. 2 and 3), normally lying on the support plane of the plant 10, parallel to the direction of feed F, by means of linear movement means 50 mounted on the translator slider 20, between a third position near to the washer machines 14, 16, 18, which allows the racks containing the instruments to be washed to move inside the washer machines 14, 16, 18, and a fourth position, distanced from the washer machines 14, 16, 18, so as to define a maneuvering interspace for the rotation of the rotating upper frame 32, as can be seen by comparing FIGS. 2 and 3.

In this form of embodiment, the base support frame 22a comprises the sliding means, in this case wheels 23, and the attachment portions 26 are provided on it so as to cooperate with the guide bar 24.

In some forms of embodiment, to allow the linear translation backward of the combined lower frame 22 and upper frame 32, the base support frame 22a comprises two guide bars 60 disposed parallel to the direction of feed F, and the lower frame 22, disposed above the base support frame 22a and below the rotating upper frame 32, is associated slidingly therewith, in this case by means of pads 62 coupled with the guide bars 60, so as to be able to be translated linearly with respect to the base support frame 22a parallel to the direction of feed F.

The lower frame 22 is solid with the rotating upper frame 32, as it is rotatably coupled with it, and therefore the linear translation backward or forward, as indicated by the arrows M in FIG. 2, in the direction of feed F of the lower frame 22, also determines a coordinated linear translation of the rotating upper frame 32.

In some forms of embodiment, the linear movement means 50 comprise a linear actuator, which is configured to act along the direction of feed F and is constrained on one side to the base support frame 22a, by means of an anchoring element 59 attached to a middle longitudinal member 22b of the base support frame 22a, and on the other side to the lower frame 22 by means of a coupling element 56 constrained to a similar anchoring element 58. In this case, the coupling element 56 is the fork type, for an articulated coupling or hinging with the anchoring element 58 of the lower frame 22, allowing a greater freedom of movement.

The linear actuator in this case comprises a cylinder 54 constrained to the base support frame 22a by means of the anchoring element 59, and a piston 56 sliding linearly inside the cylinder 54 and coupled with the lower frame 22 by means of the coupling element 56.

In some forms of embodiment, the movement of the objects toward the inside of the washer machines 14, 16 and 18, once they have been loaded onto the rotating upper frame 32 of the translator slider 20, is made possible by suitable movement means 34 (FIG. 2) mounted on board the translator slider 20, the action of which develops parallel to the direction of feed F. The movement means 34 are for example made as described in EP-A-1.787.731 in the name of the present Applicant.

Synthetically, in some forms of embodiment, the movement means 34 comprise belts or chains 36 driven by a motor 40 on board the rotating upper frame 32. The belts or chains 36 put into rotation rollers 38 disposed along the long sides 32a of the rotating upper frame 32 which allow to feed forward the racks containing the instruments to be washed.

Furthermore, the movement means 34 comprise a positioning element 43, made in this case as a blade, mounted cantilevered on a guide bar 44 disposed along one of the two long sides 32a of the rotating upper frame 32 and along which the positioning element 43 is able to slide, suitably driven by the motor 40. The positioning element 43 is provided to thrust the rack with the objects inside the washer machine, with an alternating backward-and-forward movement, but also a lifting-lowering movement with respect to the plane on which the racks containing the instruments to be washed lie, so as to selectively engage the relative rack and move it.

In some forms of embodiment, behind the battery 12 of washer machines 14, 16, 18 another translator slider is provided, indicated for convenience by the reference number 120 (FIG. 1), identical to the translator slider 20 and also mobile parallel to the direction of alignment X, but with the function of withdrawing the racks with the instruments washed, exiting from the battery 12 in the direction of feed F, and of transporting them parallel to the direction of alignment X, as indicated by arrow Q, toward other transport means, such as a rollerway 124, identical to the rollerway 24 but with the function of withdrawing and transporting the racks from the translator slider 120, for example toward the sterile sector, if necessary, or directly for packing. As can be seen in FIG. 1, the translator slider 120 also has a lower frame and rotating upper frame, indicated by the reference numbers 122, 132 and identical respectively to the lower frame 22 and the rotating upper frame 32 of the translator slider 20, and a positioning element, indicated by the reference number 143 and identical to the positioning element 43 of the translator slider 20, but with a function of withdrawing, not thrusting, from the washer machines 14, 16, 18. As for the translator slider 20, the rotating upper frame 132 is also rotatably coupled with the lower frame 122 by means of rotation means, indicated by the reference number 142 and identical respectively to the rotation means 42, to rotate between the position aligned with the direction of feed F at exit from the washer machines 14, 16, 18 and the position aligned with the rollerway 124.

Furthermore, in this case too, the combination of the lower frame 122 and the rotating upper frame 132 can be moved linearly backward-and-forward in the direction of feed F, to allow the rotation of the rotating upper frame 132 between the position aligned with the exit of the washer machines and the position aligned with the rollerway 124, without interfering with the other components of the translator slider 120 or the machines 14, 16, 18.

With the present invention it is possible to install the plant 10 even in narrow spaces where there are geometric constraints given by the main separation means, some of which can even exist prior to the installation of the plant and possibly secondary. In particular, first and second main separation means, in the drawings the two main walls 72, 78, are disposed aligned in the direction of alignment X of the washer machines 14, 16, 18 and are disposed at a reciprocal distance L. Between the first and second main separation means the battery 12 of washer machines 14, 16, 18 is disposed, and the secondary separation means, in the drawings the two secondary walls 74, 76, which extend transverse from the ends of the battery 12, respectively one toward the first main separation means, in this case the main wall 72, and the other toward the second main separation means, in this case the main wall 78, in this way delimiting the dirty sector A and the clean sector B as discussed above.

With the present invention, the distance L between the first and second main separation means, in this case the two main walls 72, 78, can be sized and minimized, in coordination with the length of the translator sliders 20, 120 and the depth D of the battery 12 of washer machines 14, 16, 18, and hence the bulk of the plant 10 can be very compact. In practice, the distance L can be compared substantially with the sum of the length of the translator sliders 20, 120 and the depth D of the battery 12, providing a maneuvering interspace, even small, for the rotation of the rotating upper frame 32 as described above.

The invention claimed is:

1. Translator slider for a washing plant to carry out at least a washing cycle on objects, which provides at least a washing and heat-disinfection operation, said translator slider being mobile in an automatic manner parallel to an alignment axis of a battery of washing and heat-disinfection machines in a front position to said battery, to receive the objects to be washed and both transport them in correspondence to an entrance of one of the machines selected on each occasion depending on a washing program set or depending on availability, and also to move them inside a desired machine in a direction of feed substantially perpendicular to said alignment axis, wherein said translator slider comprises a lower frame associated slidably to said battery of machines, in order to allow movement parallel to the alignment axis, and a rotating upper frame suitable to support the objects to be washed and which comprises a movement device that moves the objects inside the desired machine in said direction of feed, said rotating upper frame being rotatably coupled to the lower frame so as to be able to be rotated between a first position, aligned to a direction of transport of a transport device, able to direct the objects to be washed toward the translator slider, parallel to the axis of alignment, and in which said rotating upper frame is configured to receive the objects from said transport device, and a second position, aligned to said direction of feed, to direct the objects inside the desired machine.

2. The translator slider of claim 1, wherein the lower frame and the rotating upper frame are also translatable linearly with respect to a common base support frame parallel to said direction of feed via a linear movement device mounted on the translator slider, between a third position close up to the machines, in which the movement of the objects inside the machines is allowed, and a fourth position distanced from the machines, so as to define a maneuvering interspace for the rotation of the rotating upper frame.

3. Translator slider as in claim 2, wherein the base support frame comprises guide bars disposed parallel to said direction of feed and the lower frame comprises a sliding device suitable to be coupled to said guide bars, the drive of said linear movement device determining the sliding in the direction of feed of the lower frame and of the rotating upper frame with respect to the base support frame.

4. Translator slider as in claim 2, wherein the linear movement device comprises a linear actuator comprising a piston sliding in a cylinder in a direction parallel to said direction of feed, wherein the cylinder is constrained to the base support frame and the piston is coupled to the lower frame.

5. Translator slider as in claim 4, wherein the piston has a coupling element hinged to the lower frame.

6. Translator slider as in claim 3, wherein the linear movement device comprises a linear actuator comprising a piston sliding in a cylinder in a direction parallel to said direction of feed, wherein the cylinder is constrained to the base support frame and the piston is coupled to the lower frame.

7. Translator slider as in claim 6, wherein the piston has a coupling element hinged to the lower frame.

* * * * *